United States Patent
Daikuzono

(12) 
(10) Patent No.: US 6,378,133 B1
(45) Date of Patent: Apr. 30, 2002

(54) VISOR FOR INTERCEPTING LASER LIGHT FOR MEDICAL TREATMENT

(75) Inventor: Norio Daikuzono, Cincinnati, OH (US)

(73) Assignee: S.L.T. Japan Co., Ltd., Tokyo (JP)

( * ) Notice: Subject to any disclaimer, the term of this patent is extended or adjusted under 35 U.S.C. 154(b) by 0 days.

(21) Appl. No.: 09/192,567

(22) Filed: Nov. 17, 1998

(51) Int. Cl.[7] .............................. A41D 13/00; A61F 9/00
(52) U.S. Cl. ............................................. 2/9; 2/15; 2/432
(58) Field of Search ........................... 2/9, 10, 15, 432

(56) References Cited

U.S. PATENT DOCUMENTS

| | | | |
|---|---|---|---|
| 3,787,109 A | * 1/1974 | Vizenor | 350/302 |
| 4,601,533 A | * 7/1986 | Moss | 359/24 |
| 4,637,678 A | 1/1987 | Moss et al. | |
| 4,657,345 A | * 4/1987 | Gordon | 252/382 |
| 4,701,965 A | * 10/1987 | Landis | 2/428 |
| 4,917,481 A | * 4/1990 | Koechner | 350/363 |
| 4,945,573 A | 8/1990 | Landis | |
| 4,978,182 A | 12/1990 | Tedesco | |
| 5,005,926 A | * 4/1991 | Spielberger | 359/359 |
| 5,102,213 A | * 4/1992 | Lee et al. | 252/582 |
| 5,140,710 A | * 8/1992 | Rademacher | 2/432 |
| 5,173,800 A | * 12/1992 | King | 359/360 |
| 5,526,178 A | 6/1996 | Goldstein et al. | |
| 5,585,186 A | 12/1996 | Scholz et al. | |
| 5,617,250 A | 4/1997 | Hacker et al. | |
| 5,673,431 A | * 10/1997 | Batty | 2/9 |
| 5,692,522 A | * 12/1997 | Landis | 128/857 |
| 5,694,240 A | * 12/1997 | Sernbergh | 359/359 |
| 5,765,223 A | 6/1998 | McCausland | |
| 5,798,027 A | 8/1998 | Lefebvre et al. | |
| 6,243,219 B1 | * 6/2001 | Hutcheson et al. | 359/244 |

FOREIGN PATENT DOCUMENTS

WO    WO 96/18691    6/1996

* cited by examiner

*Primary Examiner*—Rodney M. Lindsey
(74) *Attorney, Agent, or Firm*—McDermott, Will & Emery

(57) ABSTRACT

The present invention relates to a visor for intercepting laser light for medical treatment, which is worn by a surgical operator or an assistant in conducting a surgical operation or diagnosis using the laser light. The visor has a frame which is provided with a shield in such a manner that the shield covers at least both eyes, and the shield is a thin plastic molded article having a reflective film on its surface for reflecting the laser light. Said shield may be detachable from a visor main body. Said reflective film comprises a multi-layered vacuum deposited film made of silicon dioxide, for example.

4 Claims, 7 Drawing Sheets

VISOR FOR INTERCEPTING LASER LIGHT FOR MEDICAL TREATMENT

TECHNICAL FIELD TO WHICH THE INVENTION PERTAINS

The present invention relates to a visor for intercepting laser light for medical treatment, the visor which is worn by a surgical operator or an assistant in conducting a surgical operation or diagnosis using the laser light.

BACKGROUND OF THE INVENTION

Direct exposure of human eyes to laser light for medical treatment gives a great influence upon a human body. It is essential then for an operator or an assistant to wear a pair of goggles-like glasses for intercepting the laser light.

The laser light intercepting goggles comprise a pair of laser light intercepting glasses which are adapted into a frame. The glasses are made of a glass material which is capable of absorbing the laser light when it transmits therethrough.

However, conventional laser light intercepting goggles in common use have such disadvantages as follows: (1) The glasses are light colored, for example green colored, which causes difficulty to a goggles wearer in identifying the true color of the tissue at an operation. (2) Since the goggles are heavy as they are made of glass, it is uncomfortable to wear them. (3) Since the goggles are held on the ears with frames like ordinary glasses, they are liable to drop and break. (4) Since the portions which cover the eyes are in the form of goggles, an operator who usually wears glasses has to wear the goggles thereon. The glasses can be superposed within the sealframe and an operation is conductible, but the operator feels very uncomfortable wearing them. (5) Since the goggles cover only the operator's eyes and their peripheries, the laser light which comes from the lateral side of the face is reflected on the inner surface of the glass of the goggles or on the inner side of the glasses in the case of an spectacled operator, so that the laser light may enter the operator's eyes. The goggles incompletely function as a shield. (6) Used goggles need to be sterilized, but they are often re-used without sterilization as they are not suitable for gas sterilization. So they are not sanitary. (7) The glass material used for goggles is expensive, so it is difficult to make disposable goggles.

Therefore it is a main object of the present invention to provide a visor for intercepting laser light for medical treatment, the visor which overcomes the above-mentioned disadvantages and has excellent advantages which will be described hereafter.

SUMMARY OF THE INVENTION

In accordance with the present invention, there is provided a visor for intercepting laser light for medical treatment, characterized in that a visor frame is provided with a shield in such a manner that the shield covers at least both eyes and in that the shield is a thin plastic molded article having a reflective film on the surface thereof for reflecting the laser light.

Said shield may be detachable from the visor main body.

Said reflective film may comprise a multi-layered vacuum deposited film made of titanium dioxide or silicon dioxide.

Said shield may cover substantially the whole surface of the face and is made of a flexible plastic material.

Said thin plastic molded article is an acrylic resin molded article, said reflective film being a multi-layered vacuum deposited film made of silicon dioxide and reflecting a light having a wave length in the range of 800 to 830 nm and transmitting a visible light therethrough, the shield having a thickness of 0.1 mm to 1.0 mm.

PREFERRED EMBODIMENTS OF THE PRESENT INVENTION

Figure 1:
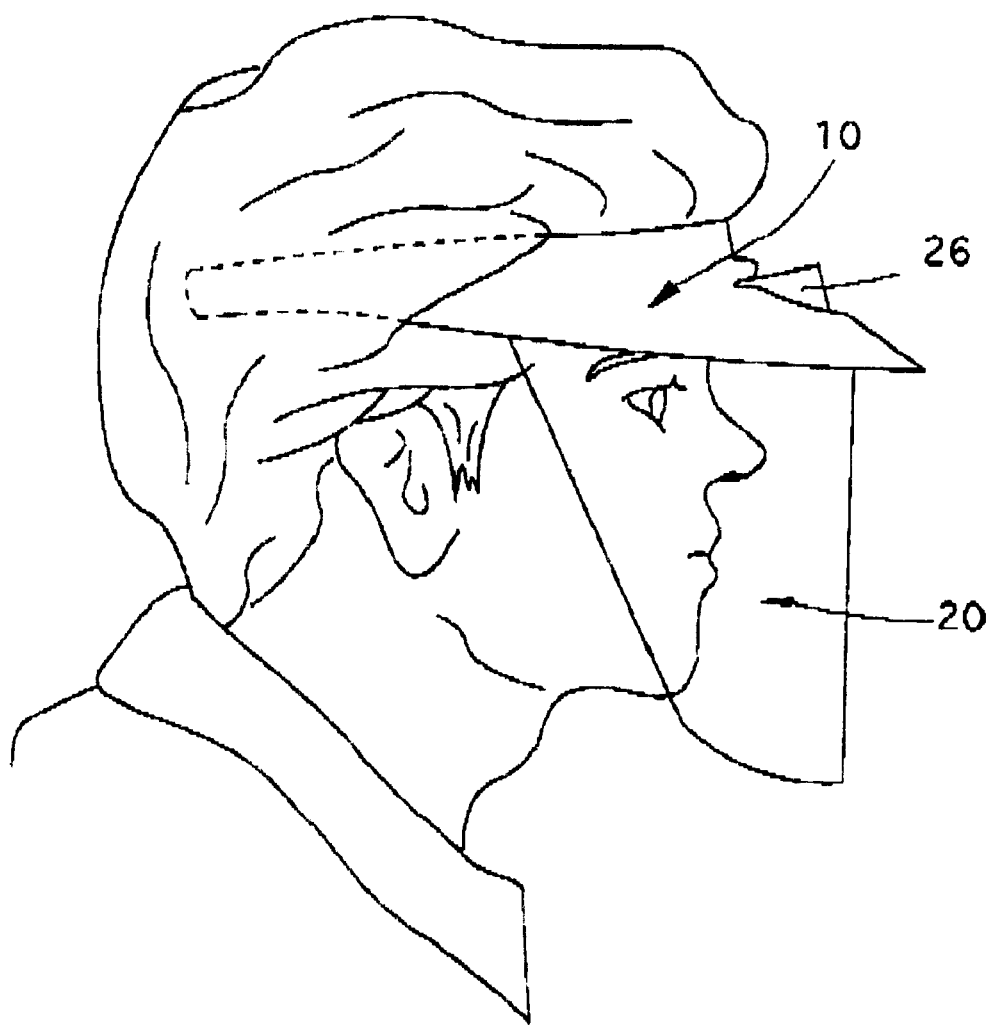
FIG. 1 is a schematic view showing how the visor for intercepting laser light for medical treatment of the present invention is worn.
Figure 2:
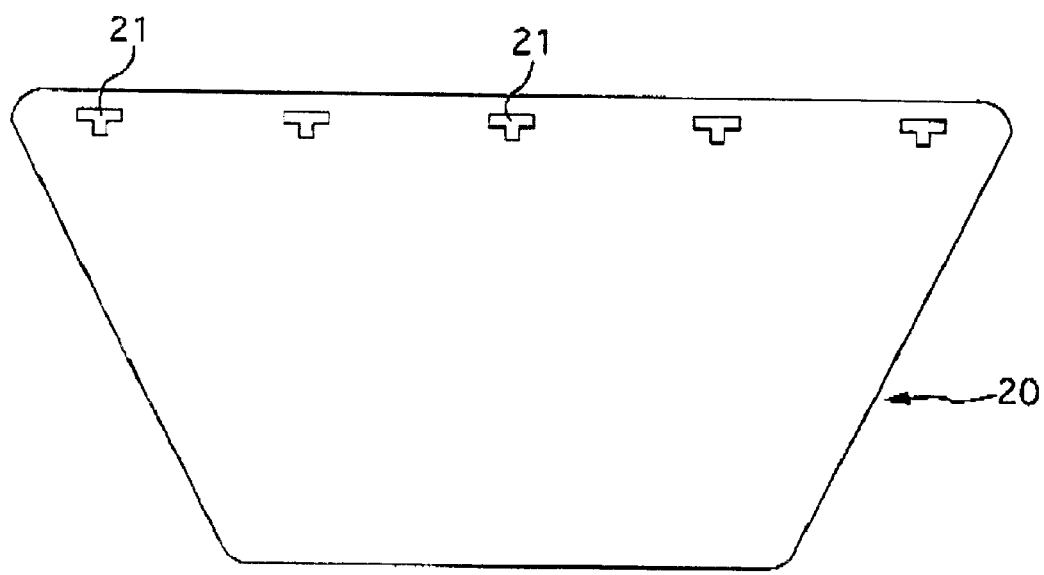
FIG. 2 is a front view of the shield.
Figure 3:
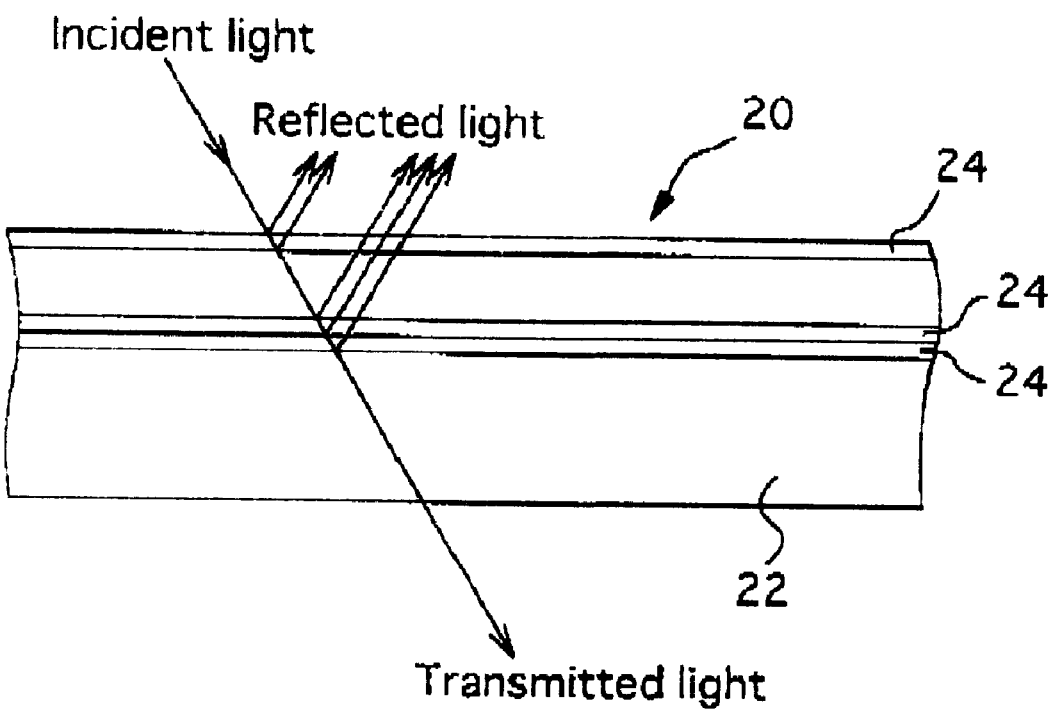
FIG. 3 is a sectional view of the shield shown in FIG. 2.

Now, the present invention will be described in detail with reference to the drawings. The visor for intercepting laser light for medical treatment of the present invention comprises a visor frame 10 and a shield 20 for covering at least both eyes as shown in FIG. 1.

The shield 20 has a reflective film 24 for reflecting laser light on the surface of a thin plastic molded member 22, such as acrylic resin. The reflective film may be formed by vacuum deposition. The film 24 is preferably multi-layered, for example, about 15 to 80 layers, since the film has less reflective effect if it is single-layered. The number of layers may be appropriately determined according to the balance between the reflectance and transmittance of the film. The film of titanium dioxide or silicon dioxide may be vacuum deposited. The reflective film is preferably capable of reflecting light having a wave length of 800 to 830 nm and of transmitting a visible light (having a wave length of, for example 400 to 700 nm). The shield preferably has a thickness of 0.1 mm to 1.0 mm.

It is preferable that the shield 20 covers not only both eyes but also the substantially whole surface of the face in order to prevent the operator from being exposed to body fluids from the patient, and conversely to prevent the patient from being exposed to operator's breath and/or saliva, and to prevent infection in a hospital.

The shield 20 is preferably detachable from the visor frame 10. If detachable, the shield 20 may be disposed of after use for one operation and replaced with the new shield 20 by mounting on the visor frame 10. The shield 20 may be used in a disposable manner.

In order to make the shield 20 detachable from the visor frame 10, the shield 20 may be formed at its upper portion with engaging holes 21, with which the hooks 12 of the visor frame 10 may be engaged. Other detachable means may be appropriately chosen.

Figure 4:
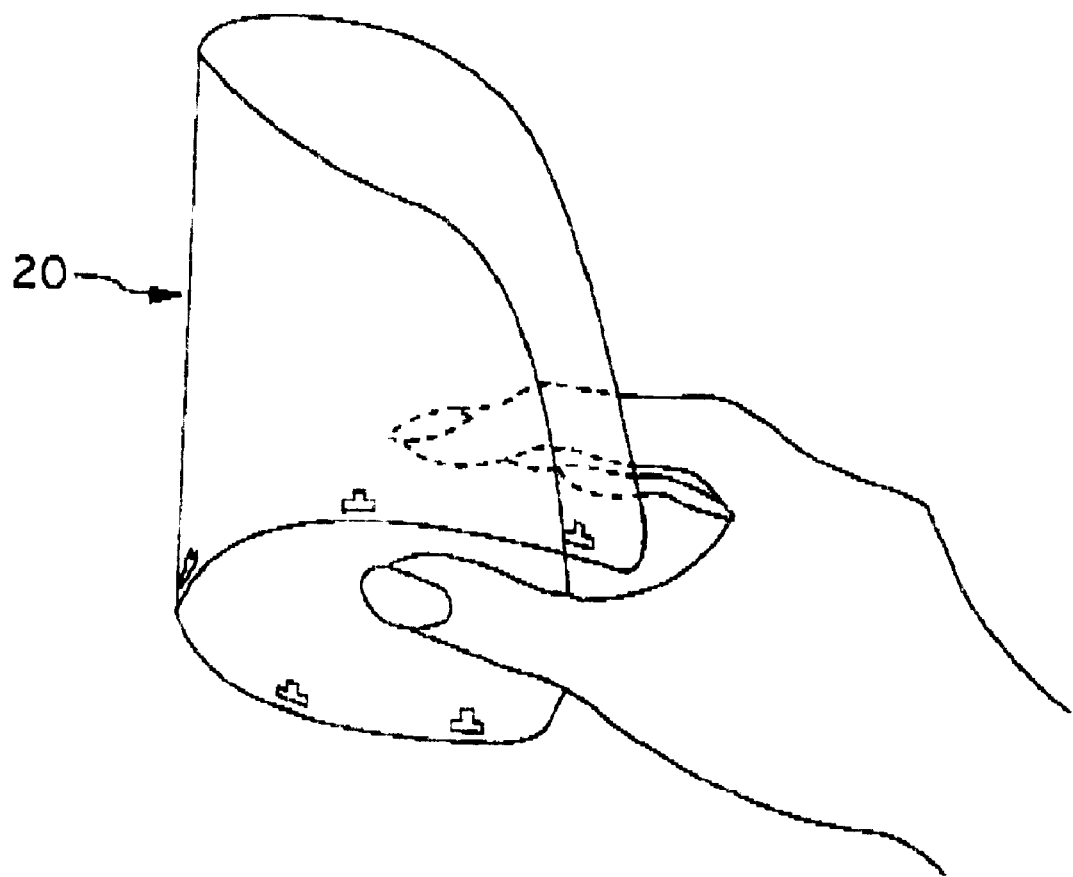
FIG. 4 is a perspective view showing that the shield is deformed to be fixed to a visor frame.
Figure 5:
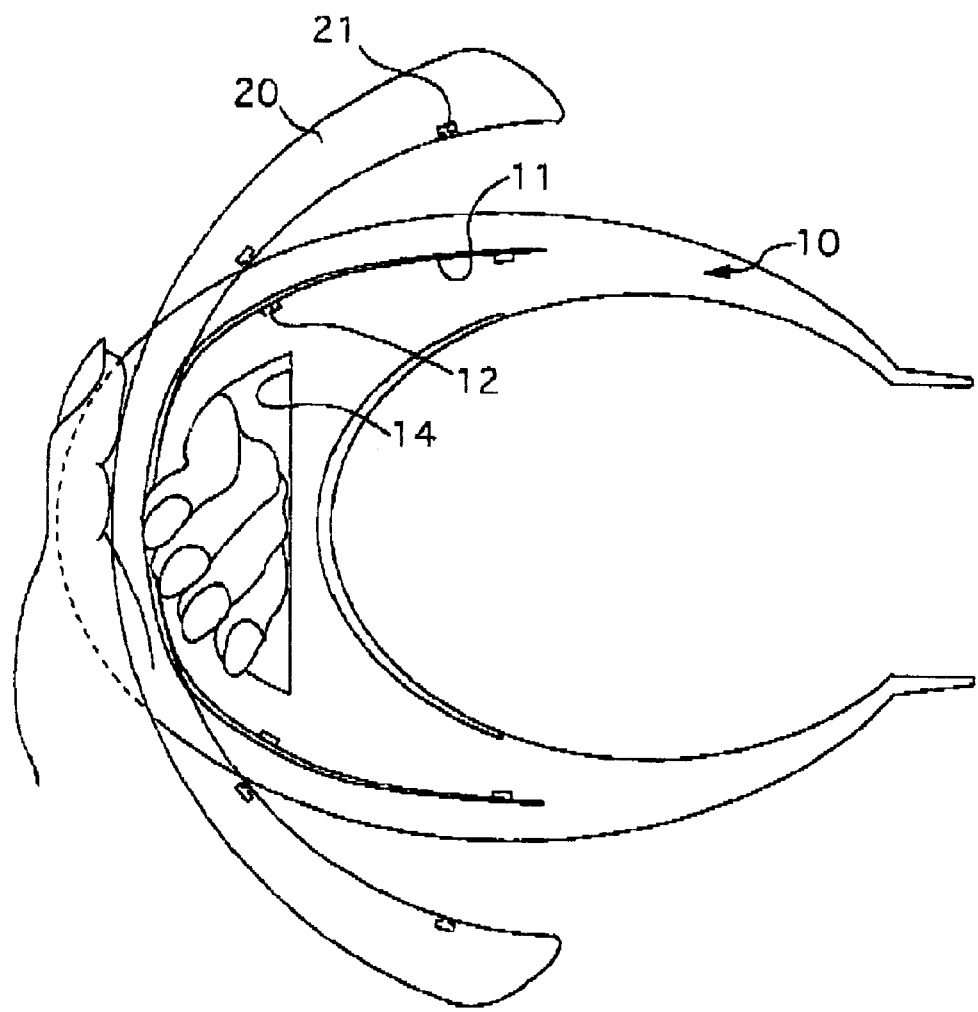
FIG. 5 is a plan view showing a step of fixing the shield to the visor frame.
Figure 6:
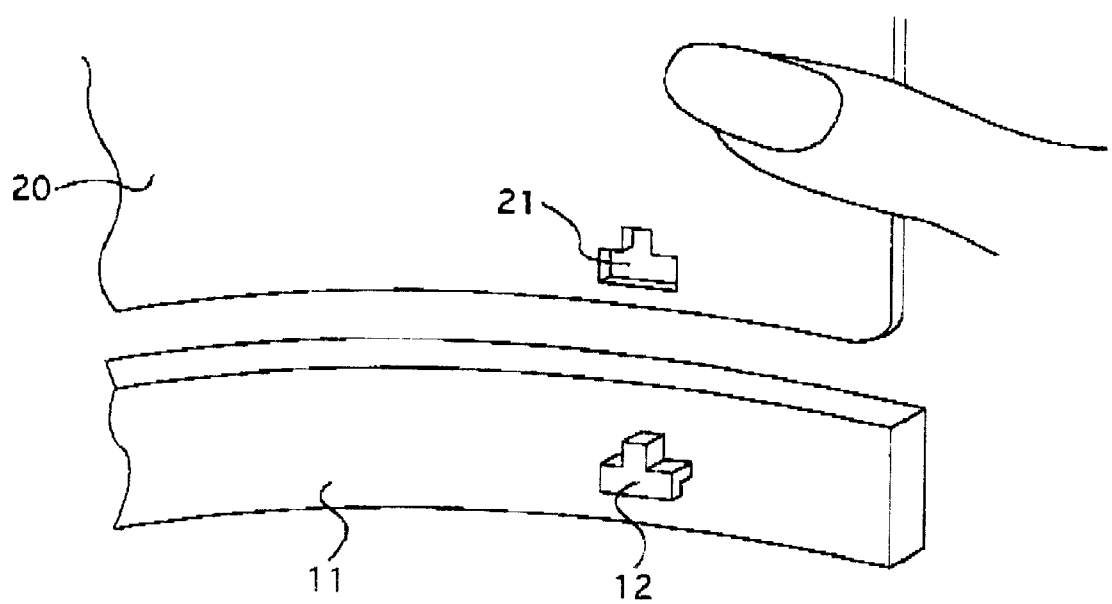
FIG. 6 is an explanatory view showing the essential part for fixing.
Figure 7:
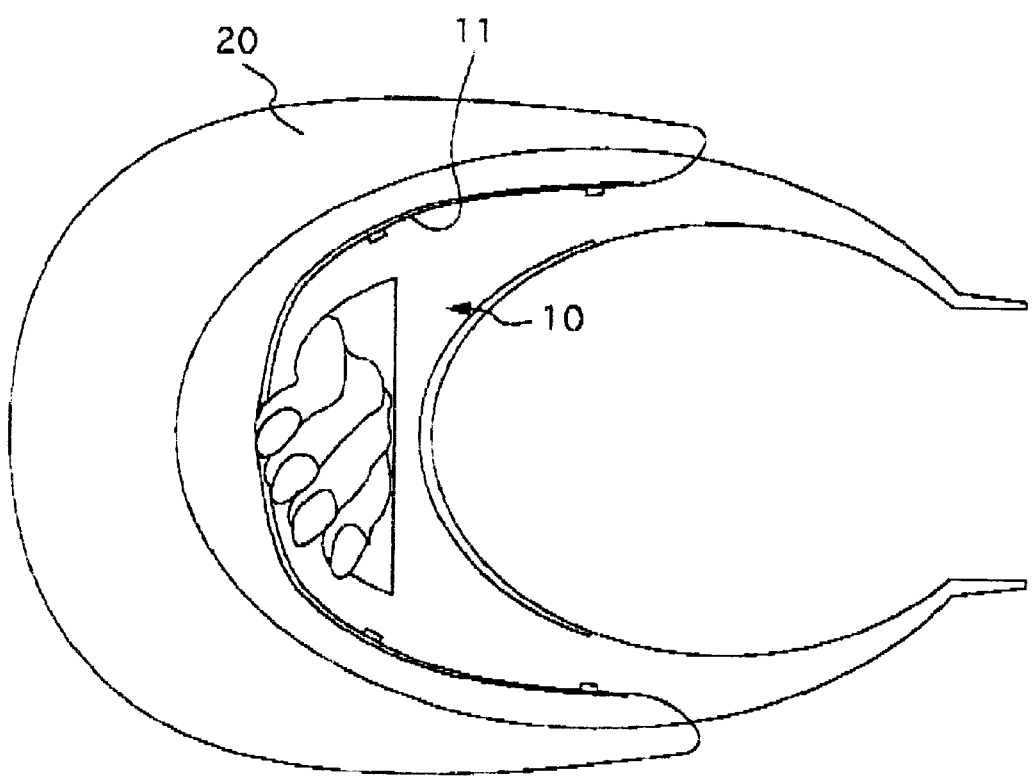
FIG. 7 is a plan view showing that the shield has completely been secured to the visor frame.

In the embodiment the shield 20 gets mounted on the visor frame 10 as follows. A protective film (not shown) which has protected the surface of the shield 20 is separated therefrom. The shield 20, being bent as shown in FIG. 4, is placed upon a holding wall 11 extending downward from the lower side of the visor frame 10 as shown in FIG. 5. The shield 20 is firmly secured to the visor frame 10 by engaging the engaging holes 21 on the upper portion of the shield 20 with the hooks 12 provided on the holding wall 11 of the visor frame 10 as shown in FIG. 6. FIG. 7 shows the state in which the shield has completely been secured to the visor frame.

The front portion of the visor frame 10 is formed with a through-opening 14 as shown in FIG. 5. Securing of the shield 20 on the visor frame 10 is facilitated by putting the fingers other than the thumb of the left hand on the holding wall 11 through the through-opening 14 while retaining the shield 20 with the left thumb. When the visor frame 10 is formed with the through-opening 14 the laser light may be incident therethrough. Then the visor frame 10 is preferably mounted with a subsidiary shield 26, like the shield 20, which has a reflective film and covers the through-opening 14.

In the foregoing embodiment the visor frame 10 is discrete from the shield 20, but they may be integral with each other. Both the visor frame 10 and shield 20 may be disposed of every time they have been used if the visor frame 10 is a plastic molded article.

As mentioned above, in comparison with conventional laser light intercepting glasses-like goggles which have been commonly used, the present invention provides advantages as follows:

(1) Since the reflective film is transparent in a visible light, the true color of the tissue to be operated can be clearly identified at a surgical operation.

(2) Since the shield is a thin plastic molded article, it is light in weight and gives a very natural feeling in wearing them.

(3) Since the visor is worn on the head, there is less risk of dropping and it will not be broken even if dropped.

(4) Even a spectacled surgical operator may wear the visor without feeling uncomfortable and obtain a wide visible field.

(5) If the visor is worn in such a manner that the shield covers the substantially whole surface of the face, the laser light coming from the lateral side of the face may be prevented from entering the eyes.

(6) The shield can be disposable because it is inexpensive and detachable from the visor main body. This obviates the necessity of sterilization treatment and makes the visor sanitary.

(7) The shield is inexpensive.

What is claimed is:

1. A visor for intercepting laser light for medical treatment, comprising a visor frame and a shield for covering at least both eyes of an operator, wherein the shield comprises a thin plastic molded article having a reflective film on the surface thereof for reflecting the laser light, said reflective film comprises a multi-layered vacuum deposited film comprising one of titanium dioxide and silicon dioxide, and said reflective film is capable of reflecting light having a wave length in the range of 800 to 830 nm and is capable of transmitting visible light.

2. The visor of claim 1, wherein said shield is detachable from the visor frame.

3. The visor of claim 1, wherein said shield covers substantially the whole surface of the face of the operator and is made of a flexible plastic material.

4. A visor for intercepting laser light for medical treatment, comprising a visor frame and a shield for covering at least both eyes of an operator, wherein the shield comprises a thin plastic molded article having a reflective film on the surface thereof for reflecting the laser light, wherein said thin plastic molded article comprises an acrylic resin, wherein said reflective film comprises a multi-layered vacuum deposited film comprising silicon dioxide and is capable of reflecting light having a wave length in the range of 800 to 830 nm and of transmitting visible light, and wherein the shield has a thickness of 0.1 mm to 1.0 mm.

* * * * *